(12) United States Patent
Schwagmeier et al.

(10) Patent No.: US 12,085,750 B2
(45) Date of Patent: *Sep. 10, 2024

(54) LATERALLY EMITTING OPTICAL WAVEGUIDE AND METHOD FOR INTRODUCING MICROMODIFICATIONS INTO AN OPTICAL WAVEGUIDE

(71) Applicant: CLINICAL LASERTHERMIA SYSTEMS GMBH, Berlin (DE)

(72) Inventors: Manuela Schwagmeier, Berlin (DE); Verena Knappe, Wentoft bei Hamburg (DE); David Ashkenasi, Berlin (DE); Hans-Joachim Cappius, Berlin (DE)

(73) Assignee: CLINICAL LASERTHERMIA SYSTEMS GMBH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/371,287

(22) Filed: Sep. 21, 2023

(65) Prior Publication Data

US 2024/0012196 A1    Jan. 11, 2024

Related U.S. Application Data

(60) Continuation of application No. 17/719,941, filed on Apr. 13, 2022, now Pat. No. 11,808,971, which is a (Continued)

(30) Foreign Application Priority Data

Jun. 19, 2015   (DE) .................. 10 2015 008 277.9
Nov. 17, 2015  (DE) .................. 10 2015 119 875.4

(51) Int. Cl.
  *G02B 6/26*      (2006.01)
  *C03C 25/6208*  (2018.01)
  (Continued)

(52) U.S. Cl.
  CPC ...... *G02B 6/02309* (2013.01); *C03C 25/6208* (2018.01); *G02B 6/001* (2013.01); *A61B 2018/2261* (2013.01)

(58) Field of Classification Search
  CPC ...... G02B 6/02309; G02B 6/001; G02B 6/26; C03C 25/6208; A61B 2018/2261
  See application file for complete search history.

(56) References Cited

U.S. PATENT DOCUMENTS 4,885,663 A   12/1989   Parker
5,226,105 A   7/1993    Myers
(Continued)

FOREIGN PATENT DOCUMENTS

CN   1672073       9/2005
DE   102 31 463 A1   1/2004
(Continued)

OTHER PUBLICATIONS

English Translation of Japanese Office Action dated Jul. 1, 2020, in connection with Japanese Application No. 2018-517473.
(Continued)

*Primary Examiner* — Jennifer Doan
(74) *Attorney, Agent, or Firm* — Norris McLaughlin, P.A.

(57) ABSTRACT

Devices and method introduce micro-modifications into an optical waveguides. The devices comprise and the methods utilize a focusing optical unit for focusing a laser pulses into a core region of the optical waveguide, at least one motor-driven adjustment device for carrying out a linear movement between the optical waveguide and a focus of the focused laser beam pulse, a holder for the optical waveguide, and a rotation device for rotating the optical waveguide, wherein the at least one motor-driven adjustment device is configured for moving the focal position through the optical (Continued)

waveguide, while the rotation device is configured to modify a rotational speed of the optical waveguide.

15 Claims, 10 Drawing Sheets

Related U.S. Application Data continuation of application No. 16/834,711, filed on Mar. 30, 2020, now Pat. No. 11,333,824, which is a division of application No. 15/737,895, filed as application No. PCT/DE2016/100272 on Jun. 15, 2016, now Pat. No. 10,641,950.

(51) Int. Cl.
*F21V 8/00* (2006.01)
*G02B 6/02* (2006.01)
*A61B 18/22* (2006.01)

(56) References Cited

U.S. PATENT DOCUMENTS

| | | | |
|---|---|---|---|
| 5,327,515 | A | 7/1994 | Anderson et al. |
| 5,432,876 | A | 7/1995 | Appeldorn et al. |
| 6,768,850 | B2 | 7/2004 | Dugan et al. |
| 6,798,960 | B2 | 9/2004 | Hamada |
| 6,832,023 | B1 | 12/2004 | Gaylord et al. |
| 6,865,320 | B1 | 3/2005 | Westbrook |
| 7,085,451 | B2 | 8/2006 | Gaylord et al. |
| 7,095,931 | B2 | 8/2006 | Sezerman et al. |
| 7,499,605 | B1 | 3/2009 | Xia et al. |
| 7,587,110 | B2 | 9/2009 | Singh et al. |
| 7,689,087 | B2 | 3/2010 | Mihailov et al. |
| 8,090,233 | B2 | 1/2012 | Sezerman et al. |
| 8,107,782 | B2 | 1/2012 | Sezerman et al. |
| 9,178,282 | B2 | 11/2015 | Mittleman |
| 10,551,624 | B2 * | 2/2020 | Rothberg ........... G02B 27/0927 |
| 11,333,824 | B2 | 5/2022 | Schwagmeier et al. |
| 11,808,971 | B2 * | 11/2023 | Schwagmeier ........ G02B 6/001 |
| 2001/0028775 | A1 | 10/2001 | Hasegawa et al. |
| 2002/0162360 | A1 | 11/2002 | Schaffer et al. |
| 2004/0071420 | A1 | 4/2004 | Sezerman et al. |
| 2004/0101242 | A1 | 5/2004 | Zervas |
| 2006/0147170 | A1 | 7/2006 | Ashkenasi et al. |
| 2006/0215976 | A1 | 9/2006 | Singh et al. |
| 2007/0165976 | A1 | 7/2007 | Arras et al. |
| 2008/0158905 | A1 | 7/2008 | Chuang et al. |
| 2008/0165565 | A1 | 7/2008 | Gunter |
| 2008/0290784 | A1 | 11/2008 | Arbab et al. |
| 2012/0224811 | A1 | 9/2012 | Geernaert et al. |
| 2014/0075850 | A1 | 3/2014 | Lai et al. |
| 2014/0078505 | A1 | 3/2014 | Lai et al. |

FOREIGN PATENT DOCUMENTS

| | | |
|---|---|---|
| JP | 2001-324643 A | 11/2001 |
| JP | 2003-255157 A | 9/2003 |
| JP | 2005-538392 A | 12/2005 |
| JP | 2006-285234 A | 10/2006 |
| JP | 2009-524082 A | 6/2009 |
| TW | 200827795 | 9/2008 |
| WO | 99/23041 A1 | 5/1999 |
| WO | 2004/013668 | 2/2004 |
| WO | 2009/104010 | 8/2009 |
| WO | 2014/120610 A1 | 8/2014 |

OTHER PUBLICATIONS

Examination Report dated Sep. 22, 2020, issued in connection with Australian Patent Application No. 2016278511.
German Office Action and English translation dated Jul. 6, 2020, issued in connection with German Patent Application No. 10 2015 119875.4.
Machine English translation of Abstract, also published as US 2008158905 A1.
Office Action dated Mar. 1, 2020, in connection with Indian Patent Application No. 201747045533.
Office Action dated Mar. 22, 2019, in connection with Chinese Patent Application No. 201680035698.8.
Written Opinion of the International Searching Authority for corresponding application PCT/DE2016/100272 dated Jun. 19, 2016. (English translation not available.).
International Search Report date Sep. 22, 2016, in connection with PCT International Application No. PCT/DE2016/100272.

* cited by examiner a)

b)

LATERALLY EMITTING OPTICAL WAVEGUIDE AND METHOD FOR INTRODUCING MICROMODIFICATIONS INTO AN OPTICAL WAVEGUIDE

This application is a continuation of U.S. patent application Ser. No. 17/719,941, filed Apr. 13, 2022, which is a continuation of U.S. patent application Ser. No. 16/834,711, filed Mar. 30, 2020, now U.S. Pat. No. 11,333,824, which is a divisional of U.S. patent application Ser. No. 15/737,895, filed Dec. 19, 2017, now U.S. Pat. No. 10,641,950, which is a § 371 U.S. National stage of PCT International Patent Application No. PCT/DE2016/100727, filed Jun. 15, 2016, which claims foreign priority benefit of German Patent Application No. DE 10 2015 008 277.9, filed Jun. 19, 2015, and German Patent Application No. DE 10 2015 119 875.4, filed Nov. 17, 2015, the disclosures of each of which patent applications are incorporated herein by reference.

FIELD OF DISCLOSURE

The invention relates to an optical waveguide and a method for introducing micro-modifications into an optical waveguide.

BACKGROUND

Optical waveguides known from the prior art generally consist of an optical waveguide core (referred to as core below) and an optical waveguide cladding (referred to as cladding below). Here, fused silica is a conventionally used production material, but the material is not restricted thereto. In order to ensure a lossless light guidance within the core, the refractive index of the cladding is less than the refractive index of the core. As result, total internal reflection can be employed at the transition between the core and the cladding such that the light is guided in the core of the optical waveguide. Sometimes further cladding is coated on the cladding. Conventional optical waveguides often additionally moreover have a so-called coating and/or a buffer, which can surround the cladding. These additional layers are usually configured in such a way that they serve, in general, for the mechanical stability of the optical waveguide and, in particular, ensure the destruction-free flexibility of the optical waveguide and the mechanical protection of the optical waveguide from external influences.

Usually, the light coupled into the core on one side and the light guided forward within the core in a virtually lossless manner is decoupled at the other end of the optical waveguide from the optical waveguide. In order to change the light path of the light within the core, it is known practice to introduce modifications into the material of the core or into the edge region between core and cladding. As a result of diffracting and/or scattering and/or refracting the light at these modifications which are describable as interferences, it is possible to modify the light path in such a way that this renders it possible to achieve targeted lateral decoupling of at least portions of the light guided in the core of the optical waveguide. If the placed modifications were introduced over a defined path along the core and/or the edge region between core and cladding, the lateral decoupling can likewise take place over this defined path.

The regions processed thus can serve as so-called fibre applicators, which are usually embodied at an end of the optical waveguide or else therewithin. It is also known to substantially realize these so-called fibre applicators by attachments placed thereon from the outside. By way of example, attachments sealed in a watertight manner, which are attached to the optical waveguide at one end of the optical waveguide, are known. Here, the end of the optical waveguide roughened by mechanical and/or chemical means or a liquid mixed with scattering particles and circulating in the attachment embodied in a liquid-tight manner serves to change the light path for the lateral decoupling of the light. By way of example, such applicators are known from documents DE 41 37 983 C2, DE 42 11 526 A1 or DE 43 16 176 A1.

A further embodiment of such an applied applicator, as is known from e.g. DE 101 29 029 A1, U.S. Pat. No. 4,660,925 or 5,196,005, is an attachment embodied as a hollow body, which is fastened to one end of the optical waveguide. Here, the hollow body is filled by a carrier matrix, e.g. a silicone gel, into which the particles serving as scattering centres have been introduced. Here, the concentration of the scattering particles can be distributed homogeneously or increase sequentially towards the end.

Such attached fibre applicators are usually produced from polymer materials and are therefore very elastic and mechanically resilient, but they also have decisive disadvantages which are substantially based on the two-part embodiment of optical waveguide and attached applicator. By way of example, the thermal capacity of attached applicators is usually substantially lower than that of the optical waveguides. Likewise, there is the risk of detachment from the optical waveguide in the case of such applicators. Usually, the various manufacturers of such attached applicators use different materials, as a result of which different thermal and mechanical properties of the applicators emerge accordingly and these are only suitable for specific wavelengths and powers. This makes interchanging between various applicators significantly more difficult, especially since these fiber applicators are optimized for specific applications. A further decisive disadvantage of attached applicators lies in the manufacturing process. Assembly is usually carried out manually and it is not automated as a result of the complexity thereof. Moreover, there can be a bubble or foreign body inclusion during the production, at which light refracts more than proportionally and this leads to so-called unwanted hotspots, and, as a result thereof, to a relatively high reject rate.

DE 44 07 547 A1 describes a method for introducing modifications into the interior of transparent materials using focused laser radiation. Here, micro-cracks which can serve as light scattering centres are generated within the transparent material with the aid of laser pulses in the nanosecond range. Precisely these micro-cracks generated thus constitute a problem when transferring this method to the application in the case of optical waveguides. This is because these cracks would lead to such material weakening within an optical waveguide which may have as a consequence the damage or even the breakage of the optical waveguide in the case of thermal or mechanical loading, e.g. when the optical waveguide is bent. Moreover, these micro-cracks are not controllable in terms of the size and the alignment in relation to the optical waveguide axis.

DE 197 39 456 A1 has disclosed a method for introducing micro-modifications acting as scattering centres into an optical waveguide. Here, the processing parameters, such as e.g. the pulse duration of the employed laser radiation, are not described in any more detail and so the exact manifestation of the arising micro-modifications is undetermined. However, the precise form has a decisive effect on the emission and mechanical stability of the optical waveguide.

Likewise, EP 1342487 B1 has disclosed a laser applicator comprising an optical waveguide having scattering means suitable for at least partly scattering the light guided in the interior out of the core of the optical waveguide, with at least some of the scattering centres forming a diffraction grating.

Although methods suitable for introducing scattering centres into the interior of the optical waveguide are described, the exact adjustment of the parameters required for controlling the manifestation of the scattering centres in a targeted manner is not described.

WO 2004/005982 A2 describes a method for the microstructuring of optical waveguides, in which use is made of ultrashort laser pulses. This method and the method specified above are worded in general terms and contain specifications in respect of the form, size and arrangement/distribution of the generated microstructures without discussing a specific design in view of the thermal and mechanical stability, both in respect of the microstructures and in respect of the processed optical waveguides.

It is known that a mechanical failure (break of the optical waveguide) may arise during bending or in the case of a different (e.g. mechanical and/or thermal) load on the optical waveguide if the tensions occurring in the interior of the optical waveguide influence the mechanical stability too strongly. Micro-cracks may already arise in the outer region of the optical waveguide cladding during the production process, in particular in the case of a drawing process. The tensions arising thus can be dissipated by way of the mechanical connection between the coating (and/or the buffer) and the lateral surface of the cladding such that there is no amplification (so-called crack growth) and hence no impairment of the mechanical stability of the optical waveguide. Furthermore, a known problem is that all in-depth processing of the interior of the optical waveguide, e.g. of the core or the cladding, impairs the mechanical stability of the optical waveguide. As a result, tensions which can still be tolerated by an unprocessed optical waveguide can lead to crack growth in the case of a processed optical waveguide, as a result of which the optical waveguide may break.

SUMMARY

It is an object of the invention to avoid or reduce one or more disadvantages of the prior art. In particular, it is an object of the invention to provide an optical waveguide suitable for radiating at least some of the light guided in the interior in the lateral direction and, at the same time, comprising a mechanical stability that is as high as possible. Furthermore, it is an object of the invention to provide a method for introducing micro-modifications into an optical waveguide, said micro-modifications being suitable for radiating at least some of the light guided in the interior of the optical waveguide in the lateral direction.

This object is achieved by an optical waveguide having the features as described and specified hereinbelow and by the features of the method described and specified hereinbelow for introducing micro-modifications.

The optical waveguide according to the invention comprises an optical wave-guiding core, a region at the distal end of the optical waveguide, wherein the micro-modifications are arranged in the region in the distal end of the optical waveguide, wherein the arrangement of the micro-modifications is ordered. Compared to an unordered or chaotic distribution, an ordered distribution of the micro-modifications renders it possible to control the tension distribution and the emission geometry in the optical waveguide. What could happen in the case of an unordered distribution is that further micro-modifications are placed precisely in the region of tension peaks, said further micro-modifications further increasing the tension. This invariably leads to further mechanical weakening in this region, which may lead to damage of the optical waveguide. If the micro-modifications are introduced in an ordered manner, the tension distribution can be actively controlled. As a result of this, it is possible for the mechanical load to be distributed by the micro-modifications in such a way that higher mechanical loads can be introduced during the operation before the optical waveguide fails when compared with optical waveguides with a chaotic distribution of the micro-modifications. Furthermore, the processing time can be reduced by a targeted arrangement of the micro-modifications since micro-modifications are only introduced wherever they also expediently contribute to the lateral emission of the light guided in the optical waveguide. This is not ensured in the case of an unordered distribution of the micro-modifications. Therefore, more micro-modifications need to be introduced in the case of an unordered distribution of the micro-modifications in order to achieve the same laterally emitted intensity as in the case of an ordered arrangement of the micro-modifications.

In a preferred embodiment of the optical waveguide, the micro-modifications are arranged on one or more parallel sectional planes, wherein the sectional planes lie perpendicular to the optical waveguide axis, and wherein the arrangement of the micro-modifications on the first sectional plane by one or more parameters from a group of parameters comprising the symmetric arrangement of the micro-modifications, the density of the micro-modifications on the first sectional plane, the density of the micro-modifications, the size of the micro-modifications, the distance of the micro-modifications from the optical waveguide axis, the distance between the micro-modifications, the alignment of the micro-modifications or other parameters, with the aid of which the position and distribution of the micro-modifications or the size or outer form thereof is described.

In a further preferred embodiment of the optical waveguide, the arrangement of the micro-modifications on a first sectional plane is repeated on at least one other sectional plane. This is advantageous in that the processing routines can be repeated and a tension distribution produced by a specific arrangement of micro-modifications can also be continued over a relatively long region.

In a further particularly preferred embodiment of the optical waveguide, the at least one other sectional plane on which the arrangement of the micro-modifications on the first sectional plane is repeated is rotated by an angle in relation to the first sectional plane.

In a further particularly preferred embodiment of the optical waveguide, the distance between the first sectional plane and the at least one other sectional plane on which the arrangement of the micro-modifications is repeated is greater than the extent of a single micro-modification.

In a further refinement of the invention, the distance between the first sectional plane and the at least one other sectional plane on which the arrangement of the micro-modifications is repeated is less than the extent of a micro-modification in the axial direction of the optical waveguide for as long as the micro-modifications do not overlap or prevent the beam passage.

In a further particularly preferred embodiment of the optical waveguide, at least one further sectional plane with micro-modifications, which has a different arrangement to the first sectional plane, lies between the first sectional plane and the at least one other sectional plane on which the arrangement of the micro-modifications of the first sectional plane is repeated.

In a further particularly preferred embodiment of the optical waveguide, the micro-modifications on the first sectional plane are arranged in a rotationally symmetric manner about the optical waveguide axis.

In a further particularly preferred embodiment of the optical waveguide, the micro-modifications are arranged on a hollow cone, with the longitudinal axis of the hollow cone lying on the optical waveguide axis.

In a further particularly preferred embodiment of the optical waveguide, the micro-modifications are arranged on a plurality of hollow cones, with the hollow cones having different diameters and the longitudinal axes of the hollow cones lying on the optical waveguide axis. The micro-modifications need not fill out the entire region of the cone up to the tip, as a result of which cut-off cones or spirals on a cone are included, among others.

In a further particularly preferred embodiment of the optical waveguide, the region at the distal end of the optical waveguide is subdivided into two portions in the direction of the optical waveguide axis, of which a first portion faces the distal end of the optical waveguide and a second portion is distant from the distal end of the optical waveguide.

It is likewise a further particularly preferred embodiment to subdivide the processed region of the optical waveguide into at least two portions, in which different ordered micro-modifications have been introduced, in each case in different alignments and embodiments.

The method according to the invention for introducing micro-modifications into optical waveguides comprises affixing an optical waveguide in one or more holders, the optical waveguide and/or the holder being mounted in a movable manner, focusing high-energy laser radiation onto a focal position by way of a focusing apparatus, the focal position being positionable in the interior of the optical waveguide, the radiation being generated by a radiation source within the scope of pulsed operation, the focusing apparatus for focusing the high-energy radiation being mounted in a movable manner, moving the focal position through the optical waveguide, wherein the movement of the focal position in the interior of the optical waveguide is selected in a targeted manner dependent on the repetition rate in order to generate a predetermined arrangement of the micro-modifications.

Preferably, the method for introducing micro-modifications into optical waveguides comprises moving the optical waveguide in a rotational movement.

In a preferred embodiment of the method for introducing micro-modifications into optical waveguides, the focal position is moved continuously through the optical waveguide.

In a further preferred embodiment of the method for introducing micro-modifications into optical waveguides moving the focal position through the optical waveguide comprises a combination of rotational movements and one or more translational movements.

In a further preferred embodiment of the method for introducing micro-modifications into optical waveguides, the movement of the focal position is correlated to the repetition rate in such a way that an ordered uniform or systematically changing arrangement of micro-modifications arises in the optical waveguide.

In a further particularly preferred embodiment of the method for introducing micro-modifications into optical waveguides, the arrangement of the micro-modifications is described by one or more parameters from a group of parameters comprising the symmetric arrangement of the micro-modifications, the density of the micro-modifications on the sectional plane, the size of the micro-modifications, the distance of the micro-modifications from the optical waveguide axis, the distance between the micro-modifications, the alignment of the micro-modifications or other parameters, with the aid of which the position and distribution of the micro-modifications or the size or outer form thereof.

In a further particularly preferred embodiment of the method for introducing micro-modifications into optical waveguides, the incoming beam direction of the radiation on the optical waveguide is at an angle between the optical waveguide axis and the incoming beam direction of unequal to 90°, in a preferred range at an angle of unequal to 90°+/−5°, in a particularly preferred range at an angle of unequal to 90°+/−10°.

In a further particularly preferred embodiment of the method for introducing micro-modifications into optical waveguides, the focusing apparatus is additionally made to vibrate in the lateral and transverse directions.

In the method for introducing micro-modifications, use is preferably made of a laser system which is able to generate ultrashort laser pulses. Here, the pulse length preferably lies in the range between 0.01 and 1000 ps, particularly preferably in the range between 0.05 and 10 ps, very particularly preferably between 50 and 500 fs. The employed wavelengths reach from the visual to the near infrared range and preferably lie between 300 and 1500 nm, particularly preferably between 500-532 nm or 1000-1064 nm. Here, the range of the employed individual pulse energies preferably lies between 1 µJ and 100 µJ, particularly preferably between 1 and 50 µJ. From this power densities of between $10^{12}$ and $10^{15}$ W/cm$^2$ emerge in the focal region.

The used or achievable repetition rate of the laser system decisively determines the processing speed when introducing micro-modifications into an optical waveguide. The higher the repetition rate is, the faster the focusing apparatus can be displaced in the case of an unchanging distance between the micro-modifications. Thus, a high repetition rate is preferable as a matter of principle. However, it should be noted here that the machining axes need to be displaceable in a correspondingly quick and precise manner. Furthermore, there may be heat accumulation within the optical waveguide in the case of very high repetition rates of greater than or equal to 1 MHz since the energy introduced into the irradiated volume of the optical waveguide can no longer be dissipated fast enough. This heat accumulation can lead to tension cracks and hence to mechanical instability or even to destruction of the optical waveguide. Therefore, a repetition rate is preferably selected in the range from 1 kHz to 1 MHz, particularly preferably between 1 and 100 kHz.

The use of ultrashort light pulses (pulse duration ≤10 ps) is advantageous in that the region of influence of the introduced heat energy remains very low, as a result of which the introduction of spatially restricted micro-modifications is made possible without damaging the surrounding material. If laser pulses in the nanosecond range are used, the energy from an individual pulse is transferred to the ion lattice of the irradiated material. Like in the case of a repetition rate that is too high, this also leads to heat accumulation in the irradiated material volume and to the formation of microscopic tension cracks, the extent of which by all means can lie in the millimetre range. This damage to the material of the optical waveguide can lead to restrictions in the mechanical stability, right up to a possible break of the optical waveguide under a mechanical and/or thermal load.

The use of ultrashort laser pulses allows a targeted change in the material properties only in the irradiated region of a few micrometres, without damaging regions surrounding this in an unwanted manner in the process. In this case, the pulse duration does not suffice to transfer the energy to the ion lattice of the surrounding material, and so there is no, or a strongly reduced, heat accumulation. As a result, it is possible to generate very small structures with very low tension in the surrounding material. Both the structures which are small as possible and the tensions which are as low as possible are necessary conditions for the targeted introduction of micro-modifications into optical waveguides. Only this allows the targeted structuring of the optical waveguide material without ensuring the mechanical stability of the optical waveguide.

A device comprising a shaft and motor system is provided for the method for introducing micro-modifications into optical waveguides. Firstly, this device serves to hold the optical waveguide and, secondly, the device allows a targeted displacement and rotation of the optical waveguide and it enables arbitrary positioning of the focus of the laser system within the optical waveguide. The method according to the invention and the associated device according to the invention allow any variation of the form, the distribution and the position of the micro-modifications within the optical waveguide. As a result of this, it is possible, for example, to influence the position or the form of the micro-modifications in a targeted manner by way of the displacement speed of the linear and rotational axes or by varying the repetition rate. The distribution of the micro-modifications is also controllable in a targeted manner, for example by way of a so-called laser-internal "pulse picking" or by way of a programmable shutter. The depth of the micro-modifications relative to the surface of the optical waveguide cladding can be influenced by a targeted movement of the focus or by a targeted adjustment of the focusing apparatus. Furthermore, an extension in depth of the individual micro-modifications can be influenced in a targeted manner by an appropriate selection of individual pulse energy, pulse duration, pulse number (individual pulse, double pulse, multiple pulse), spatial distance and/or time interval, or else by "pulse tailoring". It is likewise possible to introduce micro-modifications into the optical waveguide on the side facing away from the laser system by way of focusing through the middle of the optical waveguide. Here, it is possible additionally to use lens-like effects of the curved surface of the optical waveguide for the focusing in order thus to generate micro-modifications which have an even shorter extension in depth. The arrangement of the micro-modifications is also influenced by the focal position or the positioning of the focusing apparatus relative to the optical waveguide axis. Thus, the alignment of the micro-modification can be controlled by shifting the incoming beam position from the normal of the optical waveguide axis.

Any parameter which can be used to describe the micro-modifications, e.g. the depth position, the spatial extent, the distribution, the distance from one another, the position, the alignment or else the form of the micro-modifications, can have an influence on the mechanical stability of the optical waveguide. The smaller the spatial extent of the micro-modifications and the greater the distance between the micro-modifications, the smaller the influence is on the mechanical stability of the optical waveguide. On the other hand, it is also the case that the strength of the light decoupling caused by the micro-modifications behaves in a substantially opposite manner to the effects on the mechanical stability. Therefore, it is essential to find a compromise between the decoupled light intensity and the mechanical or thermal stability of the optical waveguide.

Various embodiments are conceivable in relation to the distribution of the micro-modifications. By way of example, it is possible to produce a deliberate irregular distribution of the micro-modifications in order to avoid grating effects, such as e.g. interferences, and in order to simultaneously ensure a uniform distribution of the decoupled light. On the other hand, a targeted regular or periodic distribution of the micro-modifications, such as e.g. a Bragg grating or else multidimensional photonic structures, is also conceivable. Moreover, the option exists of placing the micro-modifications so tightly in the interior of the optical waveguide that these modifications form a line which itself has waveguide properties. This line structure can have any length and the extent thereof relative to the optical waveguide can likewise have any embodiment; thus, for example, a straight line or spiral or helical embodiment is conceivable.

The described processing options are not restricted to a specific type of an optical waveguide. By way of a suitable adaptation of the processing parameters, it is possible to process any type of optical waveguide, such as e.g. hollow fibres, gradient index fibres, novel high-tech glass fibres without lead, photonic crystals or photonic crystal fibres.

BRIEF DESCRIPTION OF THE DRAWINGS

The present disclosure is best understood from the following detailed description when read with the accompanying Figures. It is emphasized that, in accordance with the standard practice in the industry, various features are not drawn to scale. In fact, the dimensions of the various features may be arbitrarily increased or reduced for clarity of discussion.

DETAILED DESCRIPTION

Illustrative examples of the subject matter claimed below will now be disclosed. In the interest of clarity, not all features of an actual implementation are described in this specification. It will be appreciated that in the development of any such actual implementation, numerous implementation-specific decisions may be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

Further, as used herein, the article "a" is intended to have its ordinary meaning in the patent arts, namely "one or more." Herein, the term "about" when applied to a value generally means within the tolerance range of the equipment used to produce the value, or in some examples, means plus or minus 10%, or plus or minus 5%, or plus or minus 1%, unless otherwise expressly specified. Further, herein the term "substantially" as used herein means a majority, or almost all, or all, or an amount with a range of about 51% to about 100%, for example. Moreover, examples herein are intended to be illustrative only and are presented for discussion purposes and not by way of limitation.

Figure 1:
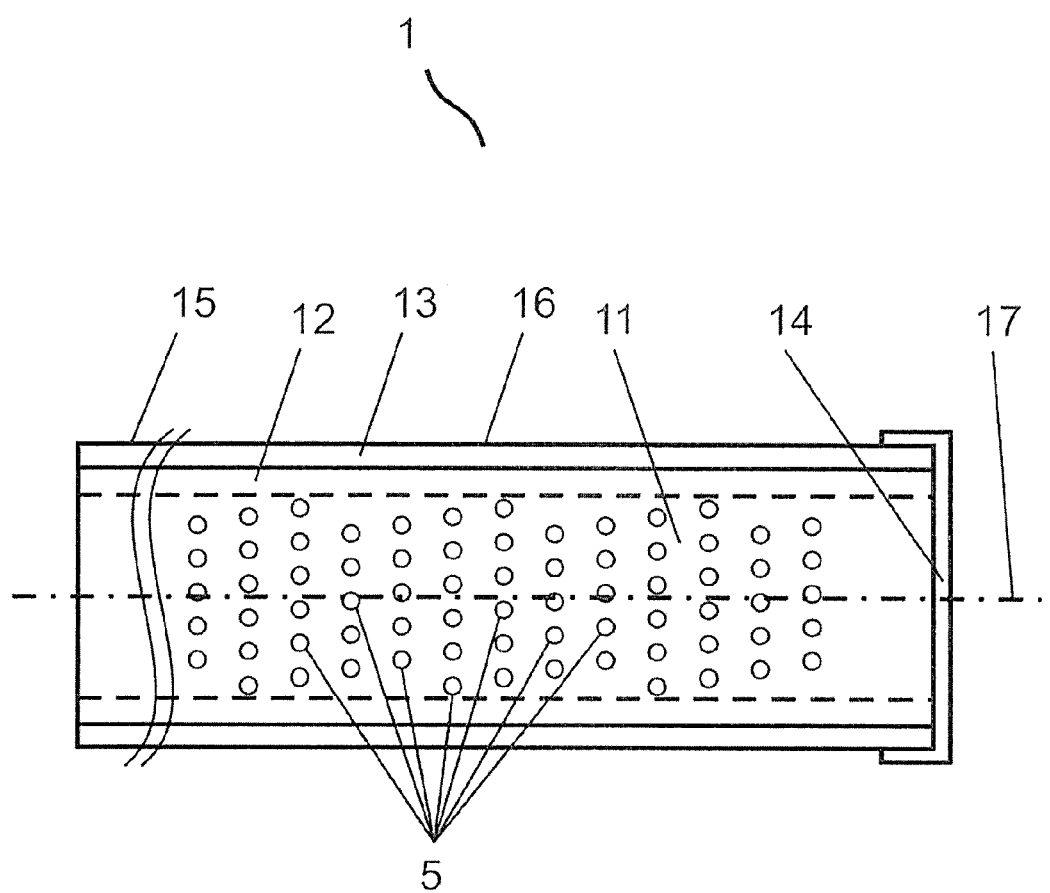
FIG. 1 shows a schematic setup of an optical waveguide with micro-modifications induced by laser radiation, according to one or more examples of the disclosure.

FIG. 1 shows a schematic illustration of the optical waveguides (1) to be machined. The optical waveguide comprises a first region (15) which is largely free from micro-modifications (5) and a second region (16) of the optical waveguide (1) into which micro-modifications (5) have been introduced. This region (16) is usually arranged at the distal end of the optical waveguide (1). Optionally, the optical waveguide can be provided with an end cap (14) which prevents light from emerging from the end region of the optical waveguide (1). By mirroring the light waves, this end cap (14) can guide the latter back to a lateral decoupling by micro-modifications. The end cap (14) can be replaced by suitable, direct mirroring of the fibre end surface; this is also in accordance with the invention. The core (11) is surrounded by cladding (12), followed by a coating and/or a buffer (13). The core (11) and cladding (12) usually consist of quartz and are doped differently. The refractive index of the cladding material is less than that of the core material; in this manner, the light can be transported in the optical waveguide (1) as a result of total internal reflection at the core-cladding transition. The cladding (12) is surrounded by a so-called coating and/or buffer (13), which takes up the tension when bending the optical waveguide (1) and therefore ensures the destruction-free resilience, and likewise serves for the protection against mechanical effects on the layers lying therebelow. For the purposes of processing the optical waveguide (1), it is possible to remove the buffer (13) that is not transparent to the selected laser wavelength such that the laser light only still needs to be focused through the cladding (12). In the case of the buffer material that is transparent to the selected laser wavelength, e.g. nylon or PTFE, the optical waveguide (1) can also be processed through the buffer (13). This is advantageous in that the processed region of the optical waveguide (1) substantially has the same increased rigidity as the rest of the optical waveguide (1).

Figure 2:
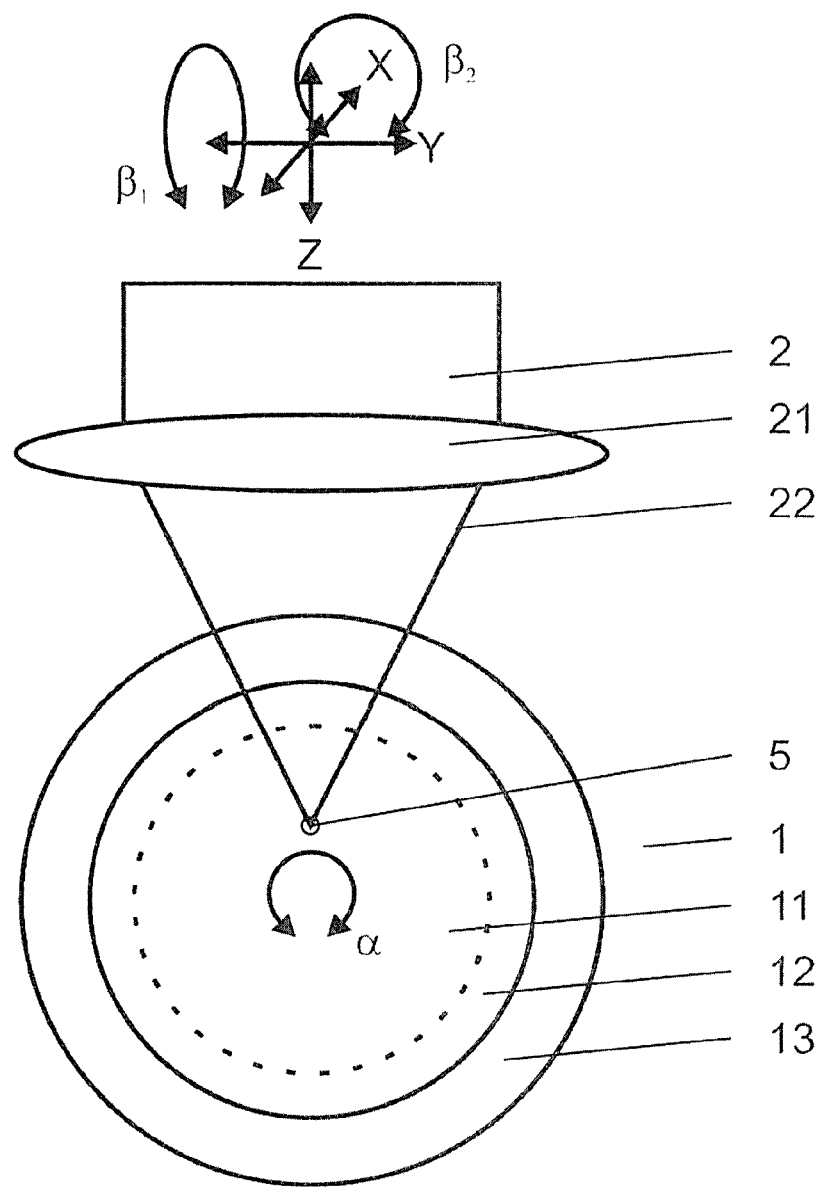
FIG. 2 shows a schematic illustration of an optical waveguide and the input coupling of focused laser light, and the possibility of relative movement between the focused laser light and the optical waveguide, according to one or more examples of the disclosure.

FIG. 2 similarly depicts the principle of coupling the focused laser light (2) into the optical waveguide (1) for introducing the micro-modifications (5). FIG. 2 shows the focusing optical unit (21) required for focusing the laser pulses into the core region of the optical waveguide (1) and the generated micro-modifications (5). In this case, important lens parameters for introducing the micro-modifications (5) into the optical waveguide (1) are the focal length and the numerical aperture (NA) of the symbolically depicted focusing optical unit (21). The focal length is selected to be as short as possible as this allows the size of the focal points to be minimized. However, in so doing, the focal length needs to be long enough to be able to focus into the core (11) through the optical waveguide cladding. In a preferred variant, the focal length of the focusing optical unit (21) lies between 1 and 5 mm. However, the use of "long-distance" microscope lenses with the work distance of greater than 5 mm is also a preferred option of implementation. An NA of the focusing optical unit (21) which is as large as possible is also advantageous since this determines the aperture angle of the focusing optical unit (21). The greater the aperture angle is, the shorter the focal region. This is of great importance as it allows the extension in depth of the introduced modifications (5) to be minimized. The larger aperture angle leads to higher beam divergence and, as a result thereof, to a quickly increasing beam diameter upstream and downstream of the focal point. This reduces the energy density in the regions upstream and downstream of the focus and therefore also reduces the absorption and the risk of damage outside of the focal region.

In a particularly preferred variant, a short focal length (f<3.1 mm) aspherical lens with a numerical aperture NA>0.68 is used as a focusing optical unit (21). In a further embodiment, use is made of a special lens (lens element system) with a high NA. It is constructed in such a way that the wavefronts of the focused laser radiation (22) have the same radius of curvature as the material surface on which they are incident. This is advantageous in that the wavefronts are not distorted (wave front distortion) when passing through the optical waveguide surface, which in turn leads to a significantly improved focusability in the material of the optical waveguide (1).

Figure 3:
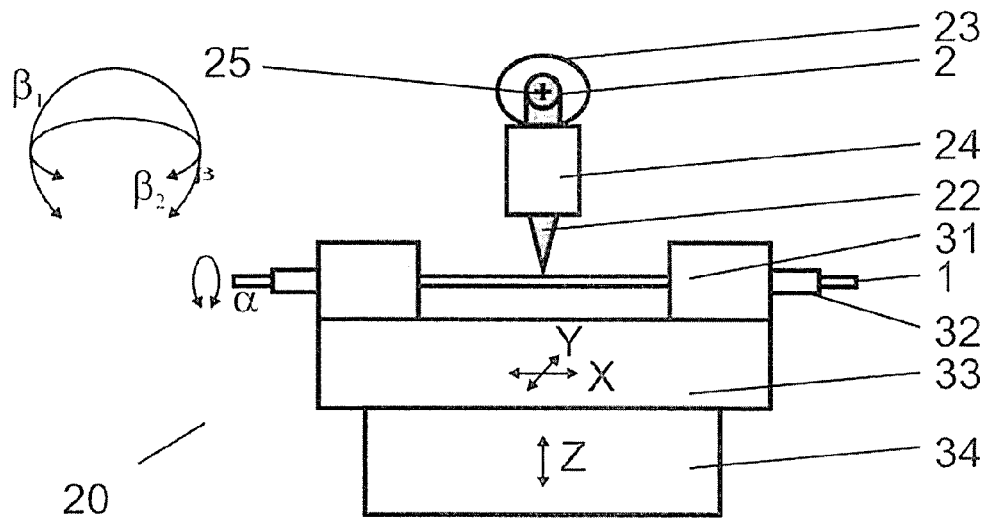
FIG. 3 shows a schematic setup of the processing device for processing optical waveguides FIG. 3a) in a frontal view and FIG. 3b) in a lateral view, according to one or more examples of the disclosure.
Figure 3:
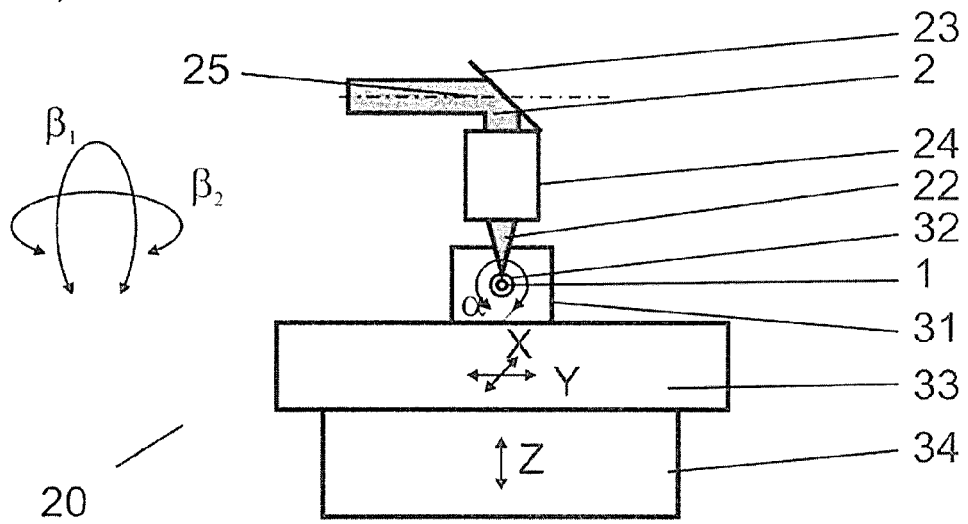

FIG. 3 shows a schematic diagram of the device according to the invention for introducing micro-modifications into optical waveguides (20). The device (20) comprises various motor-driven adjustment devices (33, 34) for carrying out a linear movement between the optical waveguide (1) and the focus of the focused laser beam (22). The movement is preferably carried out in the spatial directions (X, Y, Z) by way of linear drives (33, 34). Furthermore, the device (20) comprises the setup for coupling (23) the laser light (2) into the focusing optical unit (24). Furthermore, the device (20)

comprises the holder (32) for the optical waveguide (1) and the axes of rotation (α, β₁, β₂, β₃) for rotation of same. In contrast to the previously known solutions, it is not the focusing lens that is moved but only the optical waveguide (1). This is advantageous in that there is no need to displace or move deflection mirrors in the beam path during the processing. As a consequence, the set up or adjustment outlay for the device is significantly reduced and, at the same time, an improved long-term stability of the setup emerges since all optical elements can be securely installed in the beam path. By way of example, in the case of deflection mirrors moved by translation, even small inaccuracies or deviations in the beam path would lead to the laser beam (2) migrating on the focusing optical unit (24). As a result, the focal point migrates both in the XY-plane and in the Z-direction due to the beam passage through the focusing optical unit (24) which is at an angle relative (not perpendicular) to the optical waveguide (1). A setup with long-term stability and reproducible processing results can only be realized with much difficulty in this manner or not at all.

The Z-shaft (34) carries the further processing setup consisting of X- and Y-shaft (33), rotation device (31) and holder/guide (32) for the optical waveguides (1). It serves to move the optical waveguide (1) towards the focusing optical unit (24) or away from the latter. In this manner, it is possible to vary the distance between the focal point and the centre point of the optical waveguide (1), i.e. the depth position. The X-shaft (33) serves to displace the optical waveguide or the holder/guide (32) along the extent of the optical waveguide under the focusing optical unit (24). Thus, the maximum length of a modified region is only determined by the maximum travel of this shaft. The Y-shaft (33) moves the holder/guide (32) at right angles to the extent of the optical waveguide under the focusing optical unit (24). It serves to control the alignment of the micro-modifications (5) since the Y-shaft (33) can be used to align the focusing optical unit (24) and the optical waveguide (1) relative to one another in such a way that the laser beam (2) is incident as perpendicularly as possible on the optical waveguide surface. An oblique incidence on the surface leads to a modified beam path with a distortion of the focal region and therefore influences not only the alignment but also the form and size of the introduced modifications. The employed laser beam (20) is usually guided into the focusing optical unit (24) via a deflection mirror (23), although this is not mandatory. The optical waveguide (1) to be processed is held by a holder and guide (32) in an exact position in front of the focusing optical unit (24). This guide is cut out in the region of the processing or it is transparent to the employed laser radiation (2 and 22). The rotation device (31) serves to rotate the optical waveguide (1) about the longitudinal axis thereof. To this end, the optical waveguide (1) is fastened to the rotation device (31) by means of the tensioning device. In order to avoid excessive torsional tension of the optical waveguide (1), the latter is in this case always only rotated step-by-step by up to 360 degrees and subsequently rotated by up to 360 degrees in the opposite direction. This is realizable both for loose optical waveguide portions, e.g. finished optical waveguides, and for roll-to-roll production processes, in which the optical waveguides (1) can obtain any length.

Figure 4:
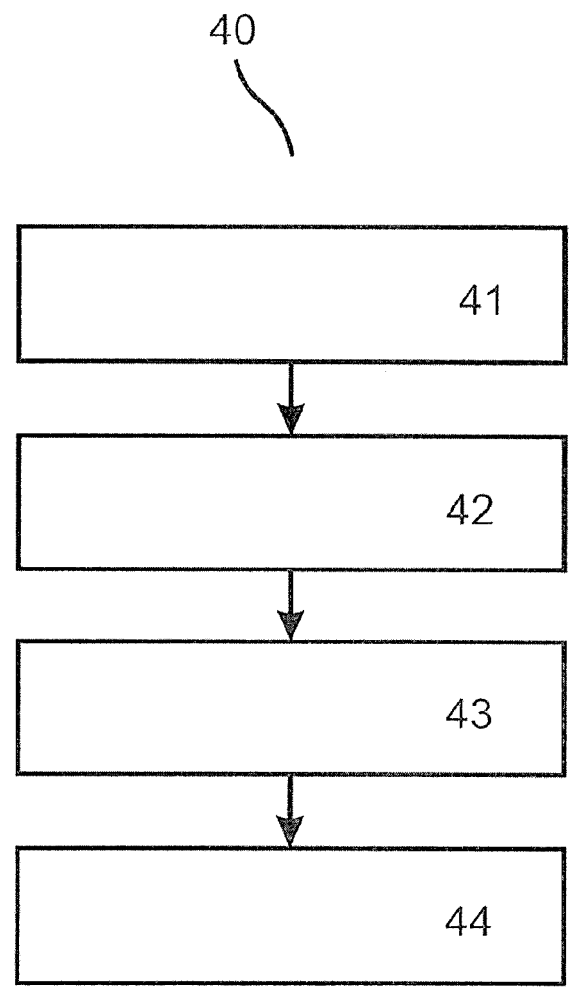
FIG. 4 shows a method for processing optical waveguides using laser radiation, according to one or more examples of the disclosure.

FIG. 4 depicts a method for processing optical waveguides (1) using laser radiation (2) in one embodiment of the invention. Initially, the optical waveguide (1) is fixed in terms of its position with the aid of a holder/guide (32) (41). The holder/guide (32) is designed in such a way that the region of the optical waveguide (1) in which the micro-modifications are intended to be generated is accessible for the laser radiation (2). The optical waveguide is mounted in such a way that it is movable in three spatial directions in relation to the focal position. This can be achieved by a movable optical unit (24) and a rigid mount of the optical waveguide (1) or by a rigid optical unit (24) and a movably arranged optical waveguide (1). The movement options comprise the three spatial directions X, Y and Z and the rotation γ about the longitudinal axis of the optical waveguide (1) and/or the rotation β₁, β₂, β₃ about one or more axes. The laser beam (2) is focused in a further method step (42). The focused laser beam (22) is positioned in such a way that, with the aid of the movement options, the position of the focus is movable through the whole region in which the micro-modifications are intended to be introduced. The focal position is moved by the optical waveguide according to a predetermined pattern (43). Preferably, use is made of a pulsed laser beam. As result of a continuous movement of the focal position through the optical waveguide (1) with a constant speed, micro-modifications (5) with an equidistant spacing in the movement direction arise. As a result of moving the focal position through the optical waveguide (1) according to a predetermined pattern, 20 or more micro-modifications (5) are generated. In a preferred exemplary embodiment of the invention, more than 36 micro-modifications (5), particularly preferably more than 360 micro-modifications (5) are generated by the movement of the focal position through the optical waveguide (1) according to a predetermined pattern. In a further method step, the movement of the focal position through the optical waveguide (1) is repeated according to a predetermined pattern (44).

In a further advantageous refinement, the focal position in relation to the optical waveguide (1) is modified by a translational and/or rotational movement after completion of the micro-modifications (5) introduced by the movement of the focal position through the optical waveguide (1) according to a predetermined pattern. This serves to avoid that, in the direction of the optical waveguide axis (17), the micro-modifications (5), which were introduced into the optical waveguide (1) in the repetition step by the movement of the focal position through the optical waveguide (1) according to a predetermined pattern, lie precisely behind the micro-modifications (5), which were introduced into the optical waveguide (1) in a first step by the movement of the focal position through the optical waveguide (1) according to a predetermined pattern.

In a further advantageous refinement of the invention, the continuous movement of the focal position through the optical waveguide (1) is carried out along the optical waveguide axis and thus subsequently results in one of the described arrangements in the sectional plane. Hence, the processing procedure within a plurality of sectional planes is thus subdivided into the generation of individual points during each passage along the optical waveguide axis (17).

In a further advantageous refinement of the invention, the continuous movement of the focal position through the optical waveguide (1) according to a predetermined pattern is superposed with a further movement. By way of example, these movements can be vibrations which serve to establish a certain lateral offset between the micro-modifications (5), which were introduced into the optical waveguide (1) in the repetition step by the movement of the focal position through the optical waveguide (1) according to a predetermined pattern, and the micro-modifications (5), which were introduced into the optical waveguide (1) in the first step by the movement of the focal position through the optical waveguide (1) according to a predetermined pattern. Preferably, the amplitude of the vibration is at least half the distance between adjacent micro-modifications (5). Thus, an ordered arrangement of micro-modifications within the meaning of the present invention arises.

The micro-modifications (5) are arranged in the optical waveguide (1) in such a way that when light passes through the optical waveguide along the optical waveguide axis (17), the micro-modifications are arranged in such a way that the light is deflected to the side as completely as possible by the micro-modifications.

In a further advantageous embodiment of the invention, the micro-modifications (5) are introduced into the optical waveguide (1) by virtue of the optical axis (25) of the laser beam (2) being positioned off the optical waveguide axis (17) on the optical waveguide (1) when irradiating the optical waveguide (1). In the case of micro-modifications (5) whose form deviates significantly from a round form, i.e. which rather have an elongate form, this renders it possible to achieve a virtually closed surface or line of micro-modifications (5) by virtue of a rotational movement only.

In a further advantageous embodiment of the invention, the micro-modifications (5) are introduced into the optical waveguide (1) by virtue of the optical axis (25) of the laser beam (2) being incident on the optical waveguide (1) at an angle ($\beta_1$, $\beta_2$, $\beta_3$) which is unequal to 90° when irradiating the optical waveguide (1). In the case of micro-modifications with an elongate form, this results in an acute angle between the orientation of the micro-modification (5) and the optical waveguide axis (17). In a further refinement of the invention, the angle ($\beta_1$, $\beta_2$, $\beta_3$) between the orientation of the micro-modification (5) and the optical waveguide axis (17) lies in a range between 10° and 80°, in a range between 20° and 70° in a preferred refinement and between 30° and 60° in a particularly preferred refinement.

Figure 5:
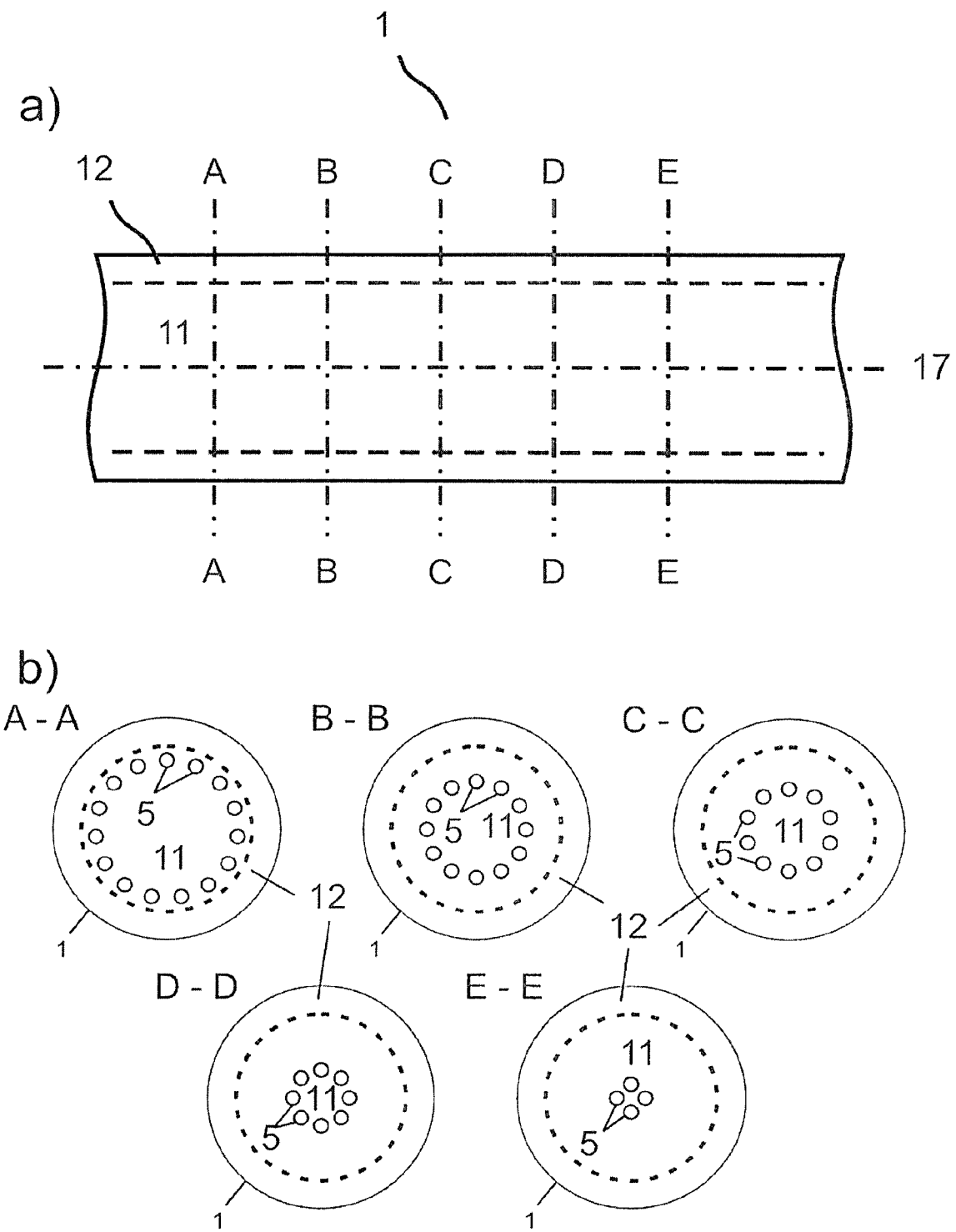
FIG. 5 shows a schematic setup of an optical waveguide with micro-modifications induced by laser radiation, FIG. 5a) showing an optical waveguide and FIG. 5b) showing cross sections along the sectional lines A-A, B-B, C-C, D-D and E-E, according to one or more examples of the disclosure.

FIG. 5 depicts a schematic setup of an optical waveguide with micro-modifications induced by laser radiation (partial figure a)) and sectional images along the sectional lines A-A, B-B, C-C, D-D and E-E (partial figure b)). The optical waveguide (1) is configured with a core region (11) and a cladding region (12). Micro-modifications (5) were introduced into the core region (12) of the optical waveguide (1) by way of irradiation in accordance with the method (40) according to the invention. The micro-modifications (5) on the depicted sectional planes (A-A, B-B, C-C, D-D and E-E) are arranged in a rotationally symmetric manner about the optical waveguide axis (17). On each sectional plane, the micro-modifications (5) have the same distance from the optical waveguide axis (17) and they are arranged on a circular arc around the optical waveguide axis (17). In the sectional plane A-A, the micro-modifications (5) lie close to the cladding (12) of the optical waveguide (1) and have a large distance from the optical waveguide axis (17). Over the course of sectional planes B-B to E-E, the distance between the micro-modifications (5) and the cladding (12) of the optical waveguide (1) increases or the distance between the micro-modifications (5) and the optical waveguide axis (17) decreases. In a further advantageous refinement of the invention, the number of micro-modifications (5) arranged on a circular arc in a sectional plane decreases with the distance of the micro-modifications (5) from the optical waveguide axis (17). This is achieved by virtue of the time interval between two laser pulses being modified and/or by virtue of the rotational speed being modified.

In a further advantageous refinement of the invention, the micro-modifications are only arranged in one of the sectional planes (e.g. A-A) depicted here, along the entire optical waveguide or in a plurality of circles within one another, i.e. as an arrangement of sectional planes depicted here that is combined in one sectional plane (e.g. A-A with C-C and/or E-E).

Figure 6:
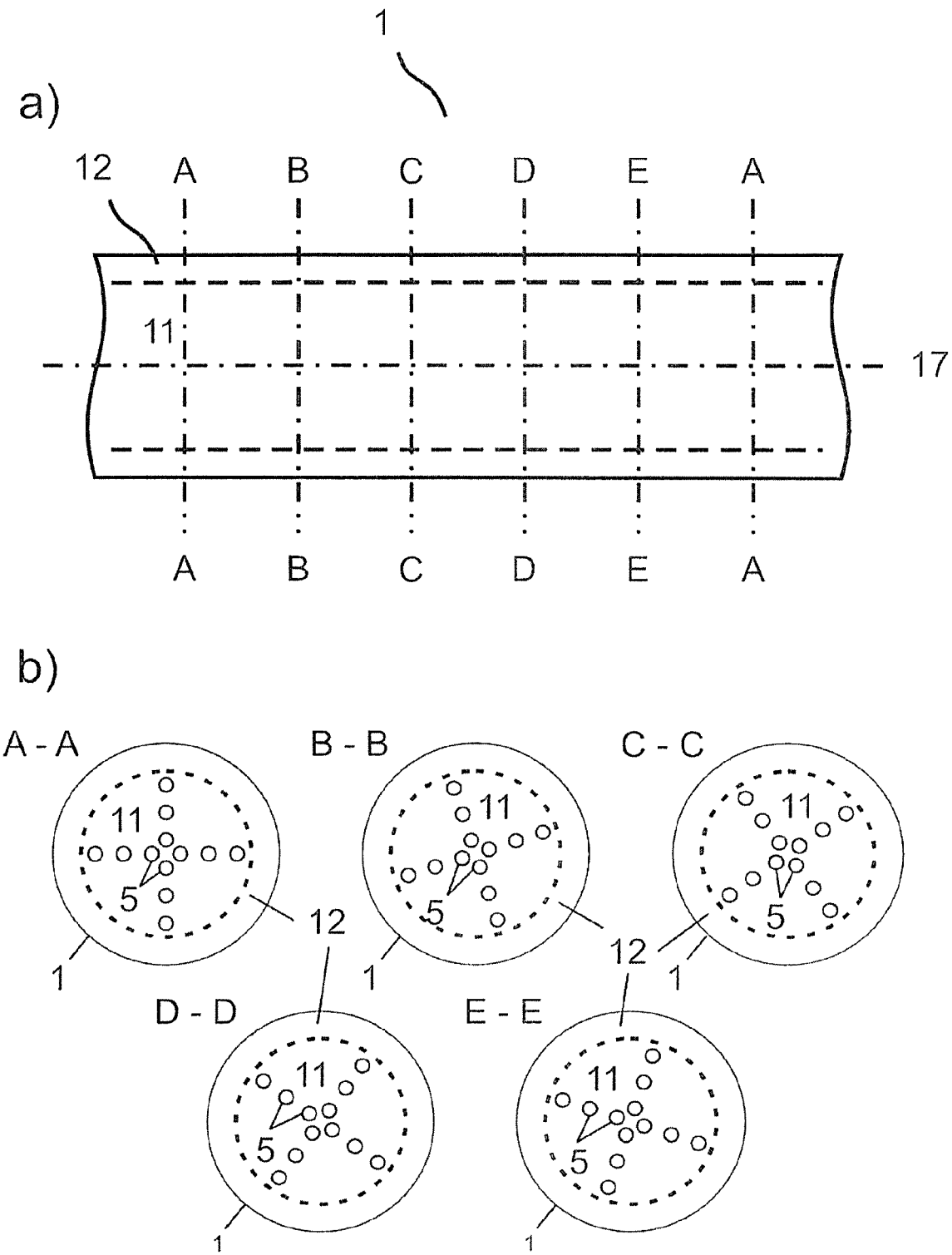
FIG. 6 shows a schematic setup of an optical waveguide with micro-modifications induced by laser radiation, FIG. 6a) showing an optical waveguide and FIG. 6b) showing cross sections along the sectional lines A-A, B-B, C-C, D-D and E-E, according to one or more examples of the disclosure.

In partial figure a), FIG. 6 shows a schematic setup of an optical waveguide with micro-modifications induced by laser radiation. Partial figure b) depicts the cross sections along the sectional lines A-A, B-B, C-C, D-D and E-E. The optical waveguide (1) is configured with a core region (11) and a cladding region (12). By way of irradiation with high-energy radiation, micro-modifications (5) were introduced into the core region (12) of the optical waveguide (1) in accordance with the method (40) according to the invention. The micro-modifications (5) on the depicted sectional planes (A-A, B-B, C-C, D-D and E-E) are arranged in a rotationally symmetric manner about the optical waveguide axis (17). The number and arrangement of the micro-modifications (5) is the same in each sectional plane. The arrangement of the micro-modifications (5) on the sectional plane B-B is rotated by an angle about the optical waveguide axis (17) in relation to the arrangement of the micro-modifications (5) on sectional plane A-A. This rotation of the arrangements of the micro-modifications (5) can be achieved by a rotation of the optical waveguide between the processing intervals for introducing the micro-modifications (5) into the optical waveguide (1). The angle of rotation of the individual sectional planes B-B to E-E in relation to the sectional plane A-A increases over the course of the sectional planes A-A to E-E. In a further advantageous refinement of the invention, the number of sectional planes A-A to E-E with different angles of rotation in a processing interval is selected in such a way that the arrangement of the micro-modifications (5) of the last sectional plane of the processing interval E-E would once again lead to the arrangement of the micro-modifications (5) on the first sectional plane A-A of the processing interval if the rotation is continued.

Figure 7:
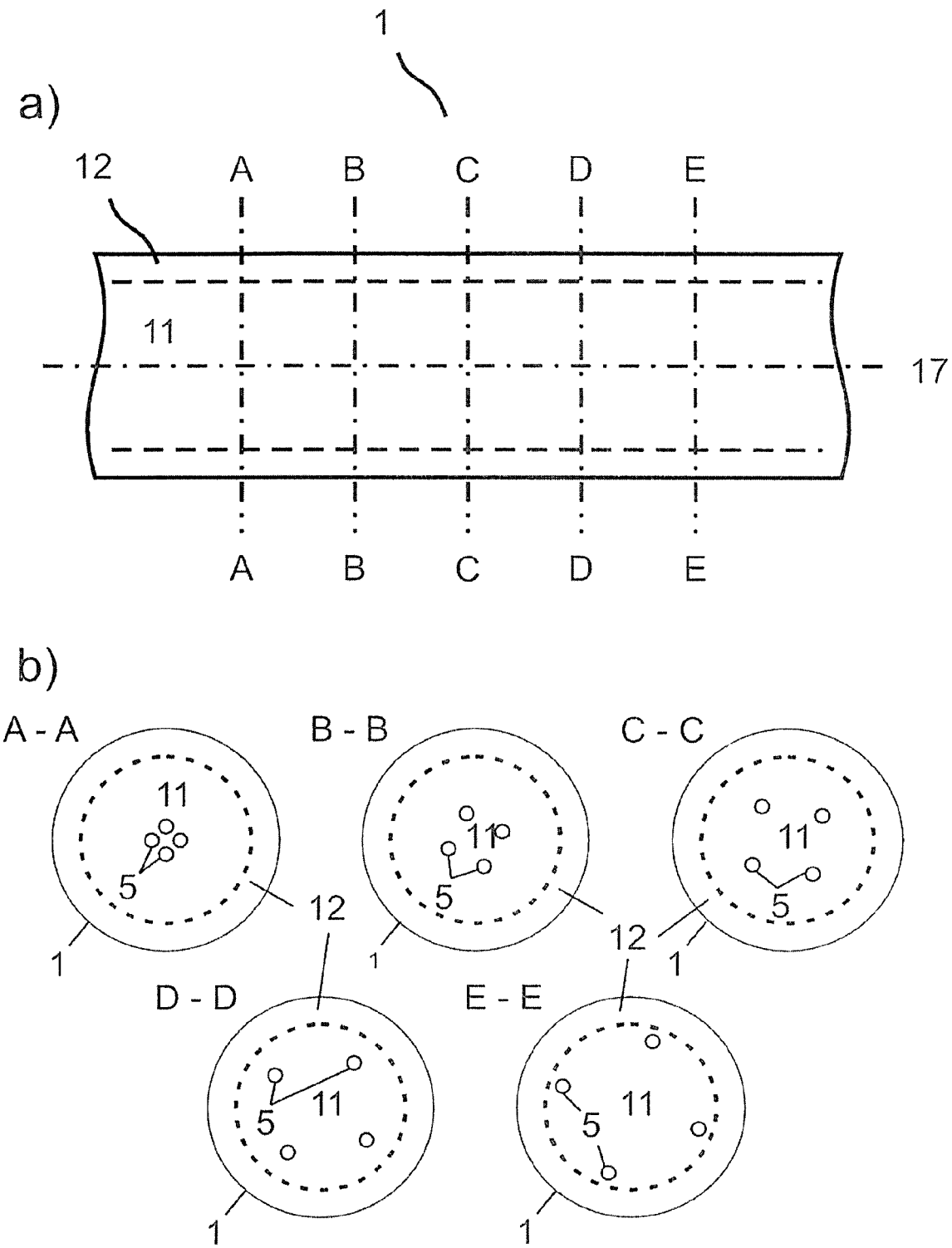
FIG. 7 shows a schematic setup of an optical waveguide with micro-modifications induced by laser radiation, FIG. 7a) showing an optical waveguide and FIG. 7b) showing cross sections along the sectional lines A-A, B-B, C-C, D-D and E-E, according to one or more examples of the disclosure.

FIG. 7 depicts a schematic setup of an optical waveguide with micro-modifications induced by laser radiation (partial figure a)) and sectional images along the sectional lines A-A, B-B, C-C, D-D and E-E (partial figure b)). The optical waveguide (1) is configured with a core region (11) and a cladding region (12). Micro-modifications (5) were introduced into the core region (12) of the optical waveguide (1) by way of irradiation in accordance with the method (40) according to the invention. The micro-modifications (5) on the individual sectional planes (A-A, B-B, C-C, D-D and E-E) are arranged in a rotationally symmetric manner about the optical waveguide axis (17). On the individual sectional planes A-A to E-E, the micro-modifications (5) are arranged on a circular arc about the optical waveguide axis (17). The radii of the circular arcs change over the course of the sectional planes A-A to E-E. Furthermore, the arrangement of the micro-modifications (5) on a sectional plane B-B is twisted by an angle about the optical waveguide axis (17) in relation to the arrangement of the micro-modifications (5) on an adjacent sectional plane A-A. A combination of a rotation about the optical waveguide axis (17) and a translation of the focused laser beam (22) in relation to the optical waveguide (1) is possible between the processing steps for arranging the micro-modifications (5) on the adjacent sectional planes in order to convert the processing steps for arranging the micro-modifications (5) in a sectional plane A-A into the processing steps for arranging the micro-modifications (5) on an adjacent sectional plane B-B.

In a further advantageous refinement of the invention, the micro-modifications are arranged in only one of the sectional planes (e.g. A-A) depicted here, along the entire optical waveguide, but rotated about the optical waveguide axis, or in a combination of sectional planes, i.e. as an arrangement of sectional planes depicted here that is combined in one sectional plane (e.g. A-A with C-C and/or E-E). In a further advantageous refinement of the invention the micro-modifications are arranged in a combination of sectional planes, i.e. as an arrangement of sectional planes depicted here that is combined in one sectional plane (e.g. A-A with C-C and/or E-E), but which changes with every further sectional plane according to the described pattern of the individual sectional planes.

Figure 8:
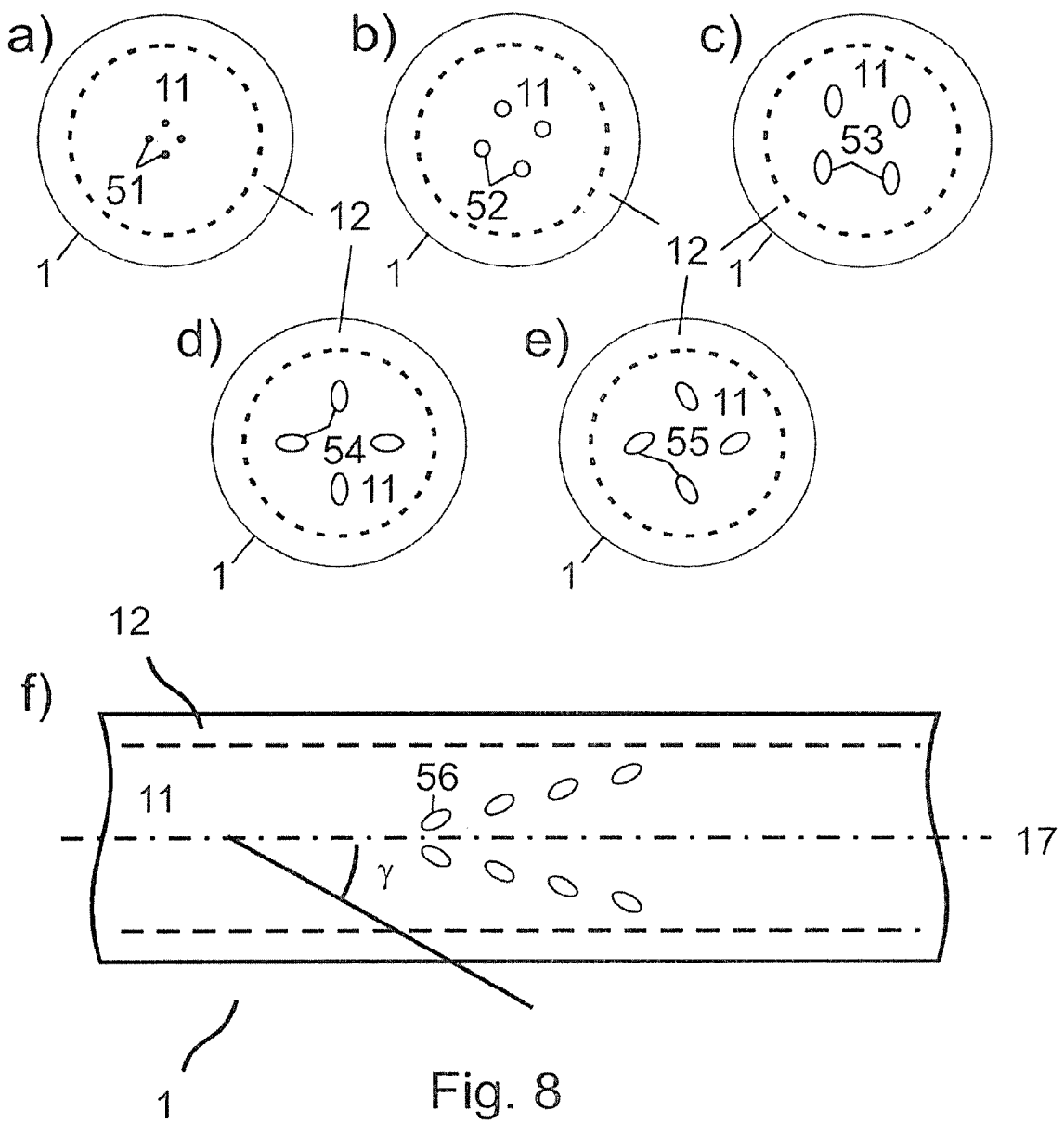
FIG. 8 shows a schematic setup of an optical waveguide with micro-modifications induced by laser radiation, FIGS. 8*a*)-8*e*) showing cross sections along the sectional lines A-A, B-B, C-C, D-D and E-E and FIG. 8*f*) showing a cross section along the optical waveguide axis, according to one or more examples of the disclosure.

On the basis of cross-sectional images with sections perpendicular to the optical waveguide axis (17) (partial figures a) to e)) and a longitudinal section along the optical waveguide axis (17) (partial figure f)), FIG. 8 in each case shows different embodiments of the invention, which depict different refinements of micro-modifications (5) induced in an optical waveguide by laser radiation. The partial figures a) and b) show micro-modifications (51, 52) with different sizes. The position of the micro-modifications can be selected independently thereof. The size of the micro-modifications (51, 52) can be influenced by the size of the focus and/or by the amount of energy introduced. The energy for an individual pulse can be between 1 and 50 µJ and the micro-modifications become larger with increasing energy, although this is dependent on the material of the optical waveguide and the laser beam quality. Furthermore, there is the option of arranging micro-modifications (5) in such a way that the boundaries thereof contact or overlap. The form of the micro-modifications (52, 53) can also be influenced by the form and positioning of the focus. Micro-modifications (53) which have an ellipsoid cross section with a large ratio of length to width arise in the case of a very elongate focus, while micro-modifications (52) which have a small ratio of length to width arise in the case of a short focal length. The form of the micro-modifications (53, 54, 55, 56) introduces a further parameter which can be used for the production of an ordered arrangement of the micro-modifications (5). Partial figures c) to f) depict different orientations of the longitudinal direction of the micro-modifications (53, 54, 55, 56). The micro-modifications (53) are all oriented in the same direction in partial figure c). This is obtained if a lateral translation in the Y-direction is carried out between optical waveguide (1) and focal position between the pulses of the laser radiation and the refraction arising as a result of the focused laser beam (22) being incident obliquely on the surface of the optical waveguide (1) is compensated for by a suitable rotation of the focused laser beam (22) about $\beta_1$, $\beta_2$, $\beta_3$. In partial figure b), the orientations of the micro-modifications (54) are arranged in a rotationally symmetric manner about the optical waveguide axis (17) of the optical waveguide (1). During machining, this is achieved by virtue of the optical waveguide (1) rotating about the optical waveguide axis (17) between the laser pulses. The micro-modifications (54) are oriented in such a way that the axis along the longitudinal direction of the micro-modification (54) through the centre of the micro-modification (54) intersects the optical waveguide axis (17) of the optical waveguide (1). Partial figure e) shows the arrangement and orientation of the micro-modifications (5) if, in addition to the processing method for partial figure d), the focused laser radiation (22) is not introduced in the direction of the optical waveguide axis (17), but the optical waveguide (1) is shifted laterally in relation to the optical waveguide axis (17). The micro-modifications (55) are then oriented in such a way that an axis along the longitudinal direction of the micro-modification (55) does not intersect the optical waveguide axis (17) of the optical waveguide (1). Partial image f) shows micro-modifications (56), the axis of which along the longitudinal direction of the micro-modification (56) through the centre of the micro-modification (56) forms an acute angle ($\gamma$) with the optical waveguide axis (17). The angle ($\gamma$) between the orientation of the micro-modification (5) and the optical waveguide axis (17) lies in a range between 10° and 80°, in a range between 20° and 70° in a preferred refinement and between 30° and in a particularly preferred embodiment. The angle ($\gamma$) can be aligned with the tip towards the distal or proximal end of the optical waveguide (1). The arrangement of the micro-modifications can be designed in a rotationally symmetric manner in relation to the optical waveguide axis (17) and can become narrower towards the distal and proximal end of the optical waveguide (1).

A movement pattern for arranging and/or orienting micro-modifications (5, 51, 52, 53, 54, 55, 56) in an optical waveguide (1) includes one or more movements from the group comprising a translation along the spatial directions X, Y and/or Z and/or rotations about the optical waveguide axis (17) and/or an axis perpendicular to the optical waveguide axis (17). At least one micro-modification (5, 51, 52, 53, 54, 55, 56) is generated in the core (11) of the optical waveguide (1) within a movement pattern. There are one or more movements from the group comprising a translation along the spatial directions X, Y and/or Z and/or rotations about the optical waveguide axis (17) and/or a spatial axis between the movement pattern being carried out a first time and the movement pattern being repeated a second and/or subsequent time. In the process, the region in which micro-modifications (5, 51, 52, 53, 54, 55, 56) were introduced into the optical waveguide (1) in a first movement pattern and the region in which micro-modifications (5, 51, 52, 53, 54, 55, 56) were introduced into the optical waveguide (1) in a second movement pattern can overlap.

Figure 9:
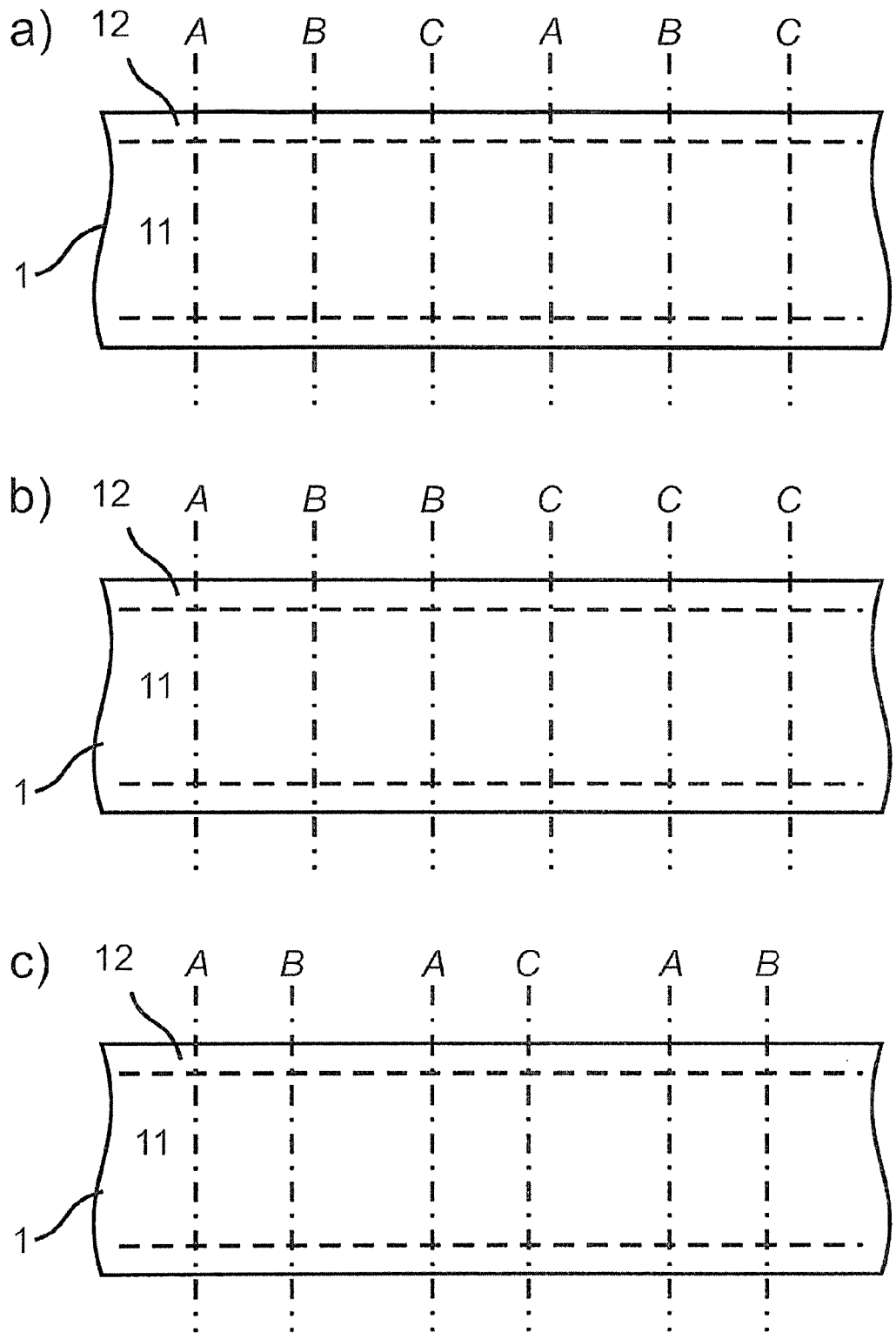
FIG. 9 shows a schematic setup of an optical waveguide with micro-modifications induced by laser radiation, FIGS. 9*a*)-9*c*) showing various periodic sequences, according to one or more examples of the disclosure.

In partial figures a) to c), FIG. 9 shows the schematic setup of an optical waveguide (1) with micro-modifications (5) induced by laser radiation. The indicated lines of intersection A, B and C denote regions in which micro-modifications (5) were introduced into the optical waveguide (1) as a consequence of a movement pattern of the focal position of the focused laser beam (22) through the optical waveguide (1). Partial figure a) depicts a sequence of three different regions (A, B, C) of arrangements of micro-modifications (5) in an exemplary manner, said arrangements repeating once more over the length of the optical waveguide. There can also be a multiple number of repeats. The regions (A, B, C) have different arrangements of the micro-modifications. Here, a region (A, B, C) is defined by one or more of the characteristics from the group comprising the size, number, orientation, form and/or arrangement of the micro-modifications (5, 51, 52, 53, 54, 55, 56). The micro-modifications (5, 51, 52, 53, 54, 55, 56) of each region (A, B, C) are induced by a movement pattern of the focal position of the focused laser radiation (22) through the optical waveguide (1) and the irradiation connected therewith. As a consequence of the different arrangements of the micro-modifications (5, 51, 52, 53, 54, 56), the arrangements of the micro-modifications (5, 51, 52, 53, 54, 55, 56) in the regions (A, B, C) are created by different movement patterns. Between the first instance of carrying out a movement pattern for producing a region (A, B, C), there are one or more movements of the focal position in relation to the optical waveguide (1) from a group comprising the three spatial directions X, Y and Z and the rotation $\gamma$ about the longitudinal axis of the optical waveguide (1) and the rotation $\beta_1$, $\beta_2$, $\beta_3$ about one or more axes.

Partial figure b) of FIG. 9 depicts a further sequence of regions (A, B, C) with the same arrangement of micro-modifications (5, 51, 52, 53, 54, 55, 56) in an optical waveguide (1) in a further embodiment of the invention. While the first region (A) is present once, this is followed by two regions with a second arrangement (B) and three regions with a third arrangement (C). In this processed optical waveguide (1) not all regions with micro-modifications (5, 51, 52, 53, 54, 55, 56) arranged according to a specific pattern are present a number of times.

Partial figure c) of FIG. 9 shows a different possible sequence of regions (A, B, C) with the same arrangement of micro-modifications (5, 51, 52, 53, 54, 55, 56) in a further refinement of the invention. While the first region (A) follows each region (A, B, C) not equal to the first region (A), the second and third regions (B, C) follow the first region (A) in alternation.

Further embodiments of the invention can be represented by arbitrary mathematical series and sequences. Here, in a further refinement of the invention, an optical waveguide (1) according to the invention comprises more than three regions (A, B, C) with different arrangements of micro-modifications (5, 51, 52, 53, 54, 55, 56). In a preferred embodiment of the invention, the optical waveguide (1) comprises more than five regions (A, B, C), in a particularly preferred embodiment comprises more than ten regions (A, B, C) with differently arranged micro-modifications (5, 51, 52, 53, 54, 55, 56).

Figure 10:
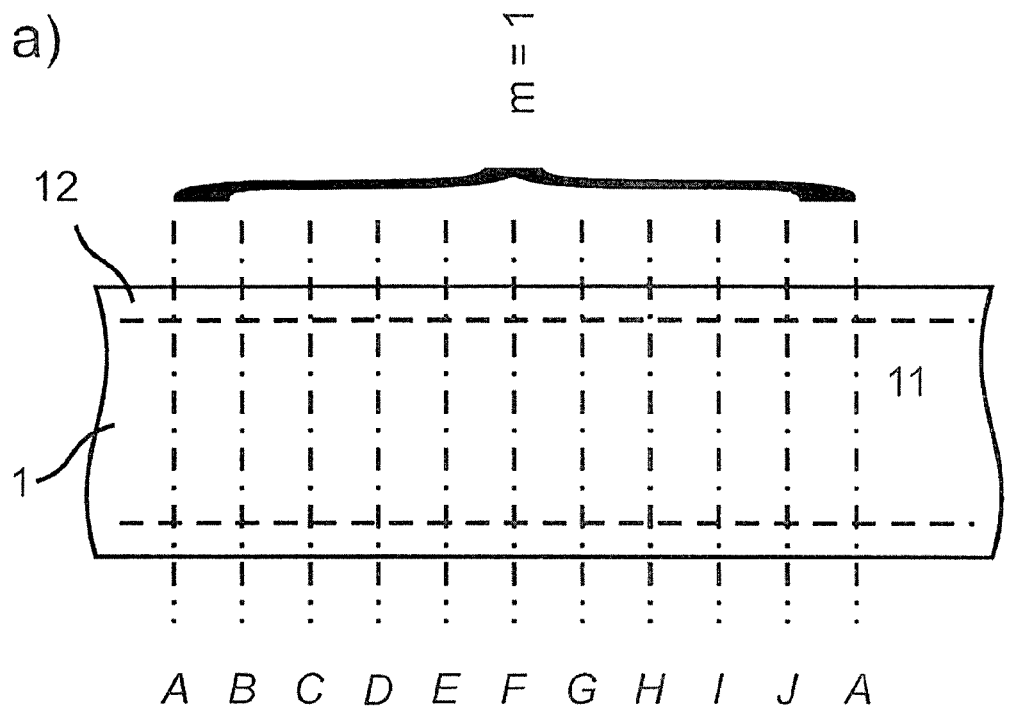
FIG. 10 shows a schematic setup of an optical waveguide with micro-modifications induced by laser radiation, FIG. 10*a*) showing a sequence of cross sections with different distributions and/or arrangements of micro-modifications, and FIG. 10*b*) showing a periodic sequence of regions with the same sequence of cross sections with different distribution and/or arrangement of micro-modifications, according to one or more examples of the disclosure.
Figure 10:
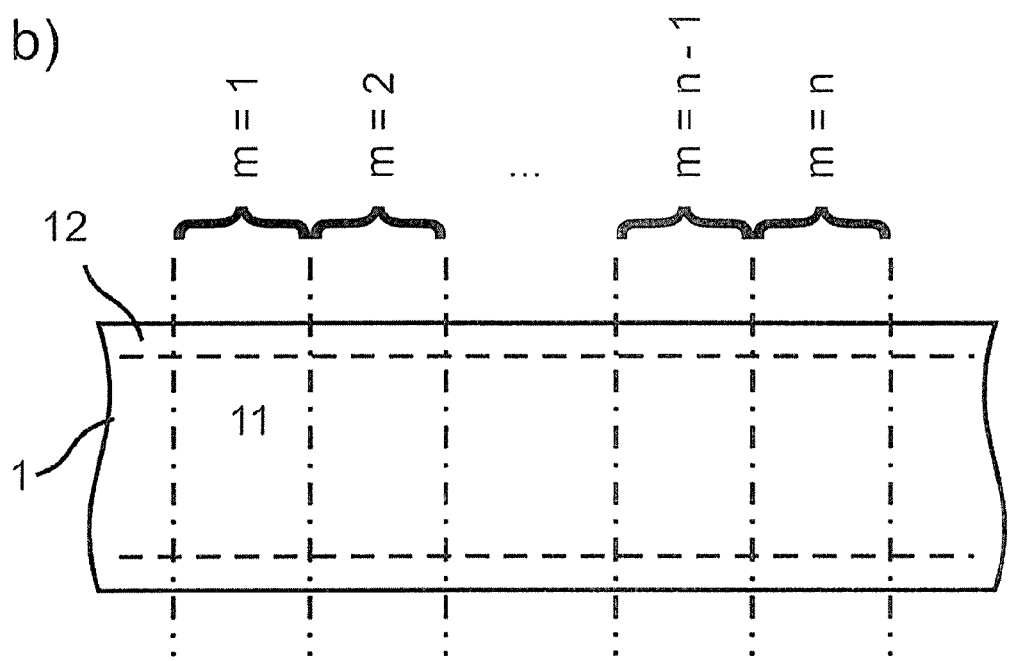

In partial figures a) and b), FIG. 10 shows the schematic setup of an optical waveguide (1) with micro-modifications (5, 51, 52, 53, 54, 55, 56) induced by focused laser radiation (22). Partial figure a) shows a sequence with a multiplicity of regions (A, B, C, D, E, F, G, H, I, J) with different arrangements of micro-modifications (5, 51, 52, 53, 54, 55, 56). This sequence of regions (A, B, C, D, E, F, G, H, I, J) with different arrangements of micro-modifications (5, 51, 52, 53, 54, 55, 56) is repeated n times (partial figure b)). Here, n, m are natural numbers. The number of repetitions of the one sequence with a multiplicity of regions (A, B, C, D, E, F, G, H, I, J) with different arrangements of micro-modifications (5, 51, 52, 53, 54, 55, 56) is denoted by m.

In a preferred embodiment of the invention, the number of repetitions of a sequence with a multiplicity of regions (A, B, C, D, E, F, G, H, I, J) with different arrangements of micro-modifications (5, 51, 52, 53, 54, 55, 56) is greater than five and greater than twenty in a particularly preferred embodiment.

In a further embodiment of the invention, the arrangement of the repetitions of the sequence with a multiplicity of regions (A, B, C, D, E, F, G, H, I, J) with different arrangements of micro-modifications (5, 51, 52, 53, 54, 55, 56) alternates in terms of the alignment of the arrangement thereof.

In a further embodiment of the invention, the arrangement of the repetitions of the sequence with a multiplicity of regions (A, B, C, D, E, F, G, H, I, J) with different arrangements of micro-modifications (5, 51, 52, 53, 54, 55, 56) is a mixed form of alternating and accordant alignments of the arrangement thereof.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific examples are presented for purposes of illustration and description. They are not intended to be exhaustive of or to limit this disclosure to the precise forms described. Obviously, many modifications and variations are possible in view of the above teachings. The examples are shown and described in order to best explain the principles of this disclosure and practical applications, to thereby enable others skilled in the art to best utilize this disclosure and various examples with various modifications as are suited to the particular use contemplated. It is intended that the scope of this disclosure be defined by the claims and their equivalents below.

LIST OF REFERENCE SIGNS

1 Optical waveguide
11 Core of the optical waveguide
12 Cladding of the optical waveguide
13 Coating, buffer and/or further coatings of the optical waveguide
14 End cap
15 Proximal end of the optical waveguide
16 Distal end of the optical waveguide
17 Optical waveguide axis
2 Laser beam
20 Device for introducing micro-modifications into an optical waveguide
21 Symbolized focusing optical unit
22 Focused laser beam
23 Deflection mirror
24 Focusing optical unit
25 Optical axis
31 Rotation device
32 Holder/guide for the optical waveguide
33 Lateral positioning device
34 Vertical positioning device
α Rotation of the optical waveguide about the optical waveguide axis
$\beta_1$, $\beta_2$, $\beta_3$ Rotation of the incoming beam direction of the laser beam
40 Method for introducing micro-modifications into optical waveguides
41 Fixing the optical waveguide in a holder
42 Focusing laser radiation in a focal position
43 Moving the focal position through the optical waveguide according to a predetermined pattern
44 Repetition of one of the movements of the focal position through the optical waveguide according to a predetermined pattern
5, 51, Micro-modification
52, 53, 54,
55, 56
γ Angle of the longitudinal alignment of the micro-modifications in relation to the optical waveguide axis
A, B, C, Radial sectional planes through the optical
D, E waveguide; these can also be inclined
F Axial sectional plane through the optical waveguide
A, B, C, Regions of the optical waveguide with micro-
D, E, F, G, H, I, J modifications are arranged therein
m Number of the repetitions of a sequence with a multiplicity of regions with different arrangements of micro-modifications
n Maximum number of repetitions of a sequence with a multiplicity of regions with different arrangements of micro-modifications.

What is claimed is:

1. A device for introducing micro-modifications into optical waveguides, the device comprising:

a focusing optical unit for focusing one or more laser pulses into a core region of the optical waveguide;
at least one motor-driven adjustment device for carrying out a linear movement between the optical waveguide and a focus of the focused laser beam pulse;
a holder for the optical waveguide; and
a rotation device for rotating the optical waveguide,
wherein the at least one motor-driven adjustment device is configured for moving the focal position through the optical waveguide, while the rotation device is configured to modify a rotational speed of the optical waveguide.

2. The device of claim 1, wherein movement of the focal position in the interior of the optical waveguide is selected in a manner dependent on a repetition rate.

3. The device of claim 1, wherein the focal position is moved continuously through the optical waveguide.

4. The device of claim 1, wherein movement of the focal position through the optical waveguide is a combination of rotational movement and translational movement of the optical waveguide.

5. The device of claim 1, wherein positioning of the focal position in the optical waveguide correlates with a repetition rate in such a way that an ordered arrangement of micro-modifications arises in the optical waveguide.

6. The device of claim 5, wherein the ordered arrangement of the micro-modifications on a sectional plane by one or more parameters from a group of parameters comprising: the symmetric arrangement of the micro-modifications, the density of the micro-modifications on the sectional plane, the size of the micro-modifications, the distance of the micro-modifications from the optical waveguide axis, the distance between the micro-modifications, the alignment of the micro-modifications or other parameters, with the aid of which the position and distribution of the micro-modifications or the size or outer form thereof is described.

7. The device of claim 1, wherein an incoming beam direction of the radiation on the optical waveguide is at an angle between an axis of the optical waveguide and the incoming beam direction of unequal to 90°.

8. The device of claim 1, wherein the focusing apparatus is made to vibrate in the lateral and transverse directions.

9. The device of claim 8, wherein an incoming beam direction of the radiation on the optical waveguide is at an angle between an axis of the optical waveguide and the incoming beam direction of unequal to 90°±5°.

10. The device of claim 8, wherein the incoming beam direction of the radiation on the optical waveguide is at an angle between the axis of the optical waveguide and the incoming beam direction of unequal to 90°±10.

11. The device of claim 1, wherein micro-modifications on a sectional plane is arranged to have at least two distances of the micro-modifications from an axis of the optical waveguide.

12. The device of claim 1, wherein micro-modifications are arranged as a spiral or helical along an optical axis of the optical waveguides.

13. The device of claim 1, wherein an arrangement of micro-modifications on a first sectional plane is repeated on at least one other sectional plane.

14. The device of claim 13, wherein the at least one other sectional plane on which the arrangement of the micro-modifications on the first sectional plane is repeated is rotated by an angle in relation to the first sectional plane.

15. A device for introducing micro-modifications into optical waveguides, the device comprising:
a focusing optical unit for focusing one or more laser pulses into a core region of the optical waveguide;
at least one motor-driven adjustment device for carrying out a linear movement between the optical waveguide and a focus of the focused laser beam pulse;
a holder for the optical waveguide; and
a rotation device for rotating the focusing optical unit around the optical waveguide,
wherein the at least one motor-driven adjustment device is configured for moving the focal position through the optical waveguide, while the rotation device is configured to modify a rotational speed of the focusing optical unit.

* * * * *